US012575814B2

(12) United States Patent (10) Patent No.: US 12,575,814 B2
Robichaud et al. (45) Date of Patent: Mar. 17, 2026

(54) FLUID SAMPLE COLLECTION SYSTEM

(71) Applicant: C. R. Bard, Inc., Franklin Lakes, NJ (US)

(72) Inventors: Jonathan Robichaud, Decatur, GA (US); Reagan H. Belflower, Atlanta, GA (US); Cecille A. Canary, Atlanta, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 927 days.

(21) Appl. No.: 17/703,819

(22) Filed: Mar. 24, 2022

(65) Prior Publication Data

US 2022/0304663 A1     Sep. 29, 2022

Related U.S. Application Data

(60) Provisional application No. 63/166,836, filed on Mar. 26, 2021.

(51) Int. Cl.
A61B 10/00          (2006.01)
A61M 25/00          (2006.01)
(52) U.S. Cl.
CPC ....... A61B 10/007 (2013.01); A61M 25/0017 (2013.01)
(58) Field of Classification Search
CPC ............. A61B 10/007; A61M 25/0017; Y10T 137/7329; Y10T 137/7336; Y10T 137/7339; F16K 21/165; F16K 21/16
See application file for complete search history.

(56) References Cited

U.S. PATENT DOCUMENTS

| | | | |
|---|---|---|---|
| 3,809,478 A | 5/1974 | Talbot | |
| 3,830,225 A * | 8/1974 | Shinnick | A61M 16/0463 |
| | | | 600/581 |
| 4,108,727 A | 8/1978 | Stiso et al. | |

(Continued)

FOREIGN PATENT DOCUMENTS

GB          840613 A  *  7/1960

OTHER PUBLICATIONS

U.S. Appl. No. 17/846,860, filed Jun. 22, 2022 Advisory Action dated Feb. 21, 2024.

(Continued)

*Primary Examiner* — Jacqueline Cheng
*Assistant Examiner* — Tho Q Tran
(74) *Attorney, Agent, or Firm* — Rutan & Tucker LLP

(57)          ABSTRACT

Disclosed herein is a fluid sample collection system including a diversion valve, a spring and a collection canister. The diversion valve includes a diversion valve housing, the diversion valve is configured to receive a volume of fluid from a first fluid line and direct the volume of fluid to either a collection canister below the diversion valve using a collection channel or to a second fluid line using a passage channel. The collection channel is located below the passage channel. The spring is coupled to the diversion valve, and configured to transition the diversion valve between a collection state and a passage state. The collection canister includes a collection canister opening. The collection canister is configured to receive the volume of fluid by gravity flow and is coupled to the diversion valve by a fluid channel.

18 Claims, 5 Drawing Sheets

(56) References Cited

U.S. PATENT DOCUMENTS

| | | | | |
|---|---|---|---|---|
| 4,423,741 | A | * | 1/1984 | Levy .................... A61B 10/007 |
| | | | | 137/625.68 |
| 5,047,211 | A | * | 9/1991 | Sloane, Jr. ......... G01N 33/4905 |
| | | | | 600/371 |
| 5,786,228 | A | * | 7/1998 | Charlton ............ A61B 10/0045 |
| | | | | 73/64.56 |
| 6,315,955 | B1 | | 11/2001 | Klein |
| 7,132,041 | B2 | | 11/2006 | Deng et al. |
| 2002/0174910 | A1 | * | 11/2002 | Willeke, Jr. ............ B60S 3/045 |
| | | | | 141/95 |
| 2003/0045840 | A1 | | 3/2003 | Burko |
| 2006/0100743 | A1 | | 5/2006 | Townsend et al. |
| 2009/0127288 | A1 | * | 5/2009 | Keller .................... B01D 46/42 |
| | | | | 222/1 |
| 2009/0149776 | A1 | | 6/2009 | Adams |
| 2010/0286559 | A1 | | 11/2010 | Paz et al. |
| 2012/0094303 | A1 | * | 4/2012 | Engel .............. G01N 33/54388 |
| | | | | 435/7.1 |

| | | | |
|---|---|---|---|
| 2015/0020588 | A1 | 1/2015 | Larson |
| 2017/0284925 | A1 | 10/2017 | Spangenberg et al. |
| 2018/0110913 | A1 | 4/2018 | Loderer et al. |
| 2020/0363395 | A1 | 11/2020 | Shimokita et al. |
| 2021/0100533 | A1 | 4/2021 | Seres et al. |
| 2021/0311018 | A1 | 10/2021 | Harrington et al. |
| 2022/0362509 | A1 | 11/2022 | Arevalos et al. |
| 2022/0362536 | A1 | 11/2022 | Nguyen et al. |
| 2022/0404333 | A1 | 12/2022 | Jagannathan et al. |

OTHER PUBLICATIONS

U.S. Appl. No. 17/846,860, filed Jun. 22, 2022 Non-Final Office Action dated Oct. 9, 2024.

U.S. Appl. No. 17/846,860, filed Jun. 22, 2022 Final Office Action dated Dec. 20, 2023.

U.S. Appl. No. 17/846,860, filed Jun. 22, 2022 Non-Final Office Action dated Oct. 5, 2023.

* cited by examiner

TO COLLECTION
CANISTER

TRANSVERSE

LONGITUDINAL

LATERAL

200

CONFIGURING THE SYSTEM FOR
FLUID SAMPLE ACQUISITION    202

ACQUIRING A FLUID SAMPLE IN THE
COLLECTION CANISTER    204

TRANSITIONING THE DIVERSION VALVE FROM THE
COLLECTION STATE TO THE PASSAGE STATE    206

PASSING A VOLUME OF FLUID THROUGH THE
DIVERSION VALVE TO THE SECOND FLUID LINE    208

FLUID SAMPLE COLLECTION SYSTEM

PRIORITY

This application claims the benefit of priority to U.S. Provisional Application No. 63/166,836, filed Mar. 26, 2021, which is incorporated by reference in its entirety into this application.

BACKGROUND

Acquiring an uncontaminated fresh sterile fluid sample from a catheterized patient can require a clinician to be present to collect the fluid sample. The clinician can remove a fluid sample from the catheter through a sample port. However, if the patient does not have a full bladder, the clinician may have to wait in order to collect a sample. Furthermore, acquiring a fluid sample may interrupt the patient's ability to void fluid until the sample is acquired. It would be beneficial to the patient and the clinician to be able to collect an uncontaminated fresh sterile fluid sample without human interaction and without interrupting the patient's ability to void fluid. Disclosed herein is a fluid sample collection system and method of use that address the foregoing.

SUMMARY

Disclosed herein is a fluid sample collection system including a diversion valve, a spring and a collection canister. The diversion valve includes a diversion valve housing, the diversion valve is configured to receive a volume of fluid from a first fluid line and direct the volume of fluid to either a collection canister below the diversion valve using a collection channel or to a second fluid line using a passage channel. The collection channel is located below the passage channel. The spring is coupled to the diversion valve, and configured to transition the diversion valve between a collection state and a passage state. The collection canister includes a collection canister opening. The collection canister is configured to receive the volume of fluid by gravity flow and is coupled to the diversion valve by a fluid channel.

In some embodiments, the collection state includes the spring being compressed relative to the passage state and the collection channel in line between the first fluid line and the second fluid line, the collection channel passing the volume of fluid from the first fluid line to the collection canister through the fluid channel.

In some embodiments, the passage state includes the spring being stretched under the weight of the collection canister having the volume of fluid within and the passage channel passes a volume of fluid from the first fluid line to the second fluid line.

In some embodiments, the collection canister having the volume of fluid within transitions the diversion valve and spring from the collection state to the passage state.

In some embodiments, the collection canister includes a vent coupled to a top side of the collection canister, the vent configured to avoid an airlock within the collection canister, the fluid channel, or the first fluid line.

In some embodiments, the vent includes a hydrophobic vent.

In some embodiments, the first fluid line is in fluid communication with a catheter.

In some embodiments, the second fluid line is in fluid communication with a fluid collection bag.

In some embodiments, the spring is secured to a stabilizing structure and the diversion valve is suspended from the spring.

In some embodiments, the collection canister includes a floater therein configured to block the collection canister opening when the collection canister is full of the volume of fluid.

In some embodiments, the collection canister includes a signaling system configured to indicate the collection canister is full of a volume of fluid.

In some embodiments, the signaling system includes volume markers on an outside surface of the collection canister.

In some embodiments, the collection canister is self-sealing.

In some embodiments, a portion of the collection channel is perpendicular to the passage channel.

Also disclosed herein is a method of collecting a fresh fluid sample from a patient without human interaction. The method includes configuring a fluid sample collection system for fluid sample acquisition, acquiring a fresh fluid sample in a collection canister, transitioning a diversion valve from a collection state to a passage state using the weight of the fresh fluid sample within the collection canister, and passing a volume of fluid through the diversion valve to a second fluid line.

In some embodiments, configuring the fluid sample collection system for fluid sample acquisition includes coupling each of a first fluid line in fluid communication with a catheter and a second fluid line in fluid communication with a fluid collection bag to a diversion valve coupling to a spring.

In some embodiments, configuring the fluid sample collection system for fluid sample acquisition includes coupling the spring to a stabilizing structure.

In some embodiments, acquiring a fresh fluid sample in the collection canister includes acquiring the fresh fluid sample with the diversion valve in the collection state, the collection state including the spring being compressed relative to the passage state, and the collection channel receiving the volume of fluid from the first fluid line and directing the volume of fluid through a fluid channel to the collection canister.

In some embodiments, acquiring the fresh fluid sample includes acquiring the fresh fluid sample in the collection canister by gravity flow.

In some embodiments, transitioning the diversion valve from the collection state to the passage state using the weight of the fluid sample within the collection canister includes the passage state having the spring being stretched under the weight of the fluid sample in the collection canister and the passage channel directing fluid from the first fluid line to the second fluid line.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

Unless defined otherwise, all technical and scientific terms used herein have the same meaning as commonly understood by those of ordinary skill in the art.

Figure 1:
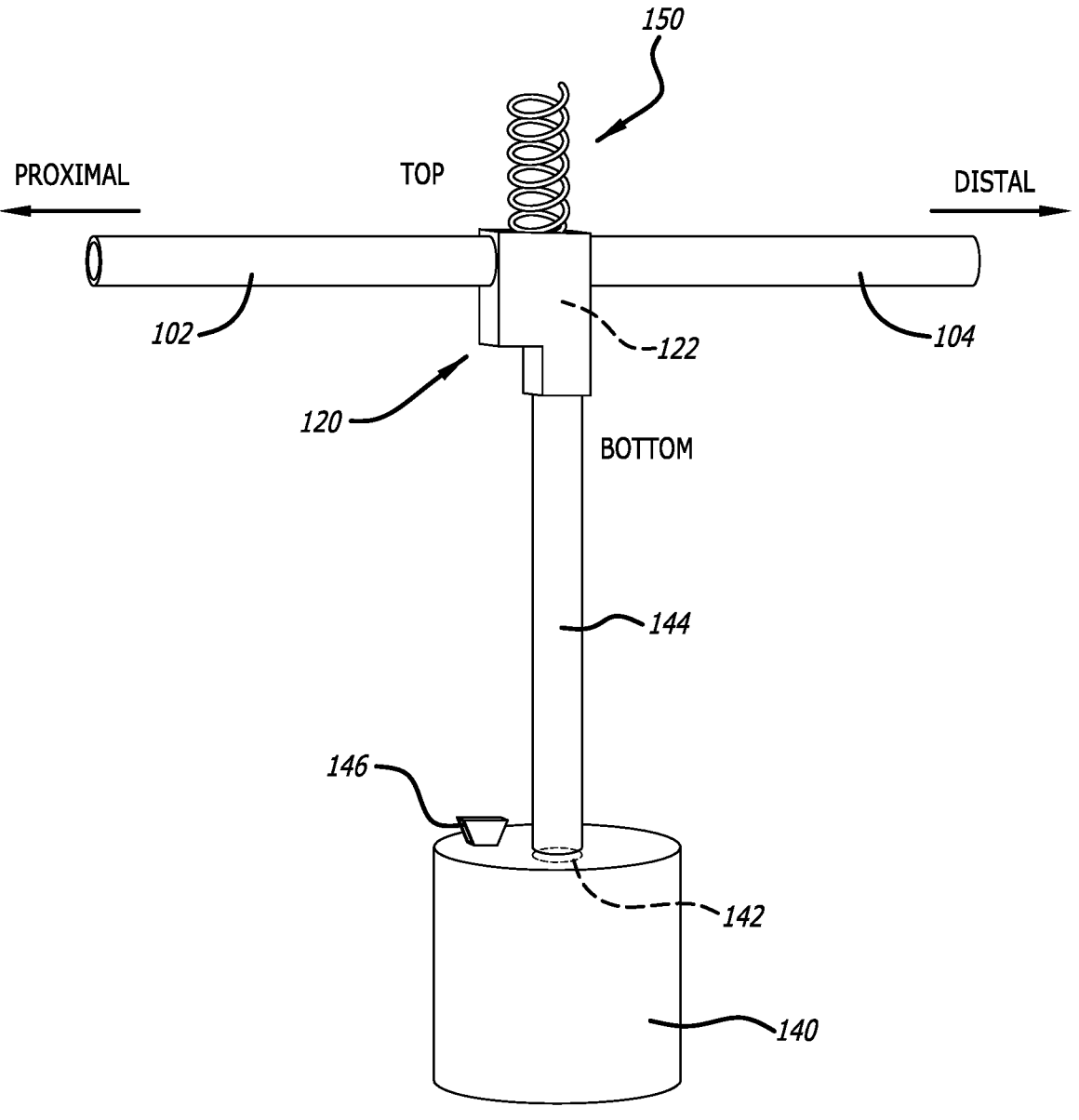
FIG. 1 illustrates a perspective view of a fluid sample collection system, in accordance with some embodiments.

FIG. 1 illustrates a side perspective view of a fluid sample collection system 100, in accordance with some embodiments. In some embodiments, the fluid sample collection system 100 may be configured to collect a fluid from an orifice in the body such as puss from a surgery site or urine from a bladder. In some embodiments, the fluid sample collection system ("system") 100 includes a diversion valve 120 in fluid communication with a first fluid line 102 and a second fluid line 104. The diversion valve 120 may be proximally coupled to the first fluid line 102 and distally coupled to the second fluid line 104. The diversion valve 120 may be configured to receive a volume of fluid from a first fluid line 102 and divert the volume of fluid to a collection canister 140 or pass the volume of fluid to the second fluid line 104. In some embodiments, the first fluid line 102 may be in fluid communication with a catheter and receive the volume of fluid from the catheter. In some embodiments, the catheter includes an indwelling urinary catheter. In some embodiments, the first fluid line 102 may be coupled to a sample port on the catheter. In some embodiments, a second fluid line 104 may be in fluid communication with a fluid collecting bag. The diversion valve 120 may include a top side and a bottom side. In some embodiments, a fluid channel 144 couples the collection canister 140 to the diversion valve 120. In some embodiments, the fluid channel 144 may detachably couple the collection canister 140 to the diversion valve 120. In some embodiments, the first fluid line 102, and the second fluid line 104 may be configured to be coupled to the diversion valve 120 through a press fit, a snap fit, an interference fit, an overlap fit or the like.

The collection canister 140 may be located below the diversion valve 120, allowing the collection canister 140 to receive the volume of fluid therein by gravity flow. The collection canister 140 may include a collection canister opening 142. In some embodiments, the fluid channel 144 may be detachably coupled to the collection canister 140 at the collection canister opening 142, allowing a clinician to remove the collection canister 140 when a fluid sample has been collected or when the collection canister 140 is completely filled with the fluid sample. In some embodiments, the fluid channel 144 may be coupled to the collection canister 140 in a press fit, an interference fit, a screw fit, a magnetic fit, a snap fit or the like. In some embodiments, the collection canister 140 may include a vent 146, configured to avoid or relieve an airlock within the system 100 including within the collection canister 140, the fluid channel 144 or the first fluid line 102. In some embodiments, the vent 146 may be located on a top side of the collection canister 140. In some embodiments, the vent 146 may include a hydrophobic vent. In some embodiments, the collection canister 140 may be configured to receive multiple sample volumes (e.g., 30 mL, 60 mL, 90 mL or the like). It can be appreciated that greater or lesser volumes are also considered. In some embodiments, the collection canister 140 is self-sealing. In some embodiments, the collection canister 140 may include a signaling system configured to indicate to a clinician that the collection canister is full of a fluid sample or that an adequate fluid sample has been obtained. For example, in an embodiment, the collection canister 140 may be clear and include a plurality of volume markings on an outside surface of the collection canister 140, configured to indicate the volume of fluid acquired within the collection canister 140 to a clinician. In an embodiment, the collection canister opening 142 may include a collection canister plug, configured to seal the collection canister opening 142 for transporting the collection canister 140 after the collection canister 140 has been detached from the fluid channel 144. In some embodiments, the collection canister 140 may be disposable or reusable. In an embodiment, the collection canister 140 may include a floater within the collection canister 140 configured to block the fluid channel 144 when the collection canister 140 is full of fluid.

In some embodiments, the diversion valve 120 may include a diversion valve housing 122. The system 100 includes a spring 150 configured to couple the diversion valve housing 122 to a stabilizing structure (e.g., a hospital bed, a pole cart, a medical device, or the like). In some embodiments, the spring 150 may be configured to allow the diversion valve 120 to be suspended from the stabilizing structure. The spring 150 may be configured to maintain the diversion valve 120 and collection canister 140 in an upright position. The spring 150 may be coupled to the top side of the diversion valve 120. The spring 150 may be configured to be compressed or stretched under the weight of a fluid sample within the collection canister 140. The spring 150 may be configured to transition the diversion valve 120 between a passage state and a collection state, that will be described in more detail herein.

Figure 2:
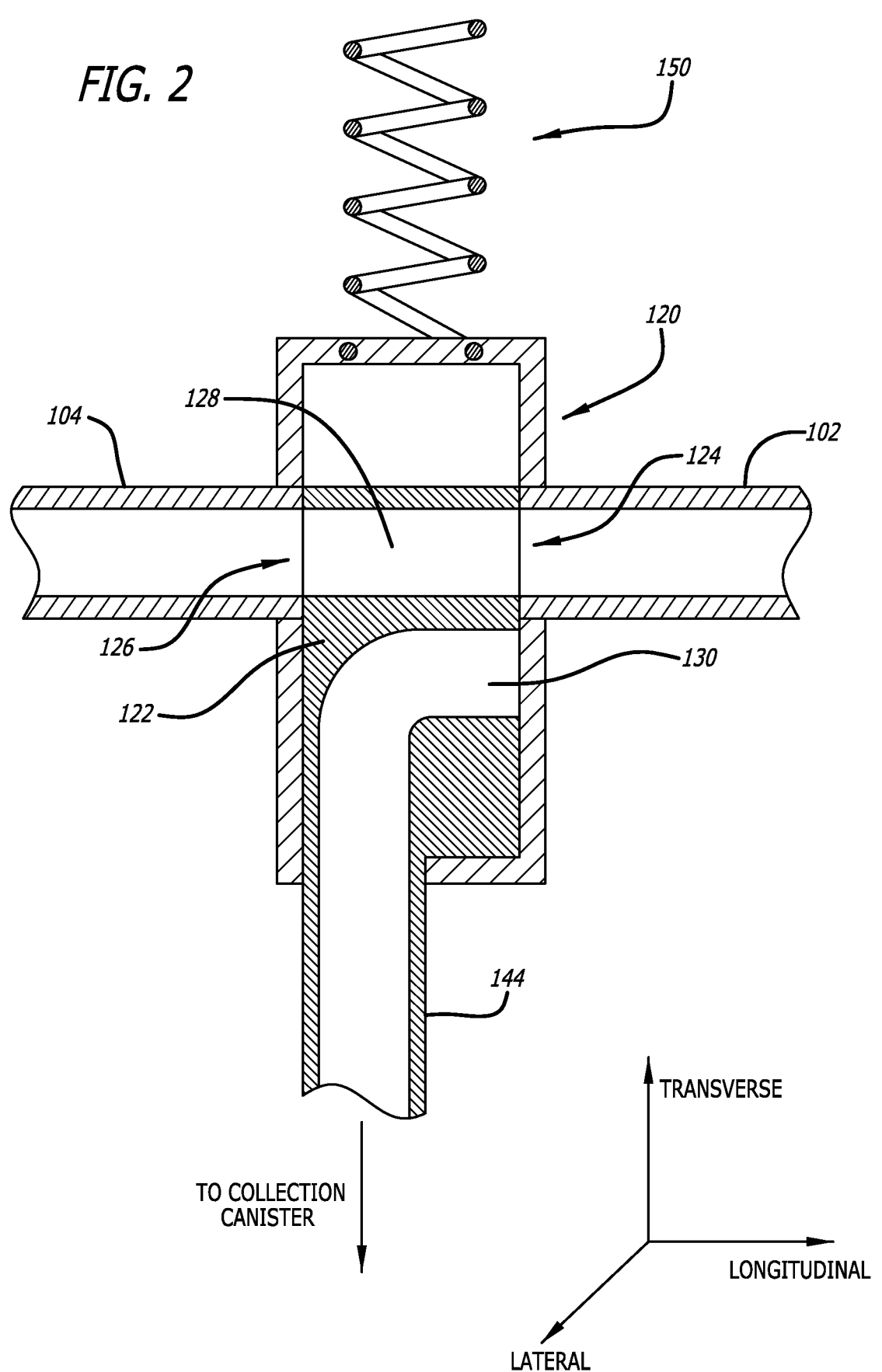
FIG. 2 illustrates a cross sectional side view of a diversion valve, in accordance with some embodiments.

FIG. 2 illustrates a cross sectional view of the diversion valve 120, in accordance with some embodiments. The diversion valve housing 122 may include a first fluid line opening 124 and a second fluid line opening 126. The first fluid line opening 124 and second fluid line opening 126 allow the diversion valve housing 122 to transition between the passage state and the collection state, while maintaining fluid flow between either the first fluid line 102 and the collection canister 140 or the first fluid line 102 and the second fluid line 104. The diversion valve 120 may include a passage channel 128 and a collection channel 130. The passage channel 128 may be located above the collection channel 130. In some embodiments, the passage channel 128 may be configured to maintain fluid communication between the first fluid line 102 and the second fluid line 104. The collection channel 130 may be configured to maintain fluid communication between the first fluid line 102 and the collection canister 140. Either the passage channel 128 is used to maintain fluid communication through the diversion valve 120 or the collection channel 130 is used to maintain fluid communication through the diversion valve 120. In some embodiments, a portion of the collection channel 130 may be configured to be perpendicular to the passage channel 128, as illustrated in FIG. 2. The diversion valve housing 122 may be configured to allow the passage channel 128 and collection channel 130 to slide along a transverse axis, seamlessly directing fluid to the collection canister 140 or to the second fluid line 104. In some embodiments, the diversion valve housing 122 within the diversion valve 120 may be configured to slide along the transverse axis to allow the passage channel 128 and the collection channel 130 to direct fluid to the collection canister 140 or to the second fluid line 104. In some embodiments, the entire diversion valve 120 may be configured to slide along the transverse axis to allow the passage channel 128 and the collection channel 130 to direct fluid to the collection canister 140 or to the second fluid line 104.

In the passage state, the spring 150 is stretched under the weight of the fluid sample within the collection canister 140, the passage channel 128 is in line between the first fluid line 102 and the second fluid line 104 and receives fluid from the first fluid line 102, passes the fluid through the passage channel 128 to the second fluid line 104 coupled to the fluid collecting bag. The entirety of the volume of fluid passing through the passage channel 128 is passed to the second fluid line 104. In the collection state, the spring 150 is compressed relative to the passage state, and the collection channel 130 is in line between the first fluid line 102 and the second fluid line 104, receives fluid from the first fluid line 102, passes the fluid through the collection channel 130 and to the collection canister 140 through the fluid channel 144. The spring 150 may be coupled to a top side of the diversion valve housing 122 or to a top side of the diversion valve 120. The spring 150, along with the weight of the fluid sample within the collection canister 140, may be configured to transition the diversion valve 120 between the collection state and the passage state. As the collection canister 140 is filled with fluid, the weight of the collection canister 140 increases. The spring 150 transversely stretches due to the increase in weight of the fluid sample within the collection canister 140, pulling the spring 150 downward. As the spring 150 stretches, the diversion valve 120 or the diversion valve housing 122 moves transversely downward, removing the collection channel 130 from fluid communication between the first fluid line 102 and the second fluid line 104 and placing the passage channel 128 in fluid communication between the first fluid line 102 and the second fluid line 104.

In some embodiments, the spring 150 may be biased to the passage state or the collection state.

In some embodiments, the spring 150 may be configured to transition the diversion valve 120 from the collection state to the passage state when the collection canister 140 receives a defined volume of fluid. For example, the spring 150 may transition the diversion valve 120 when the collection canister 140 has received 30 mL of fluid therein. In some embodiments, when the collection canister 140 is acquiring the volume of fluid, the diversion valve 120 may transition only from the collection state to the passage state. In some embodiments, once the diversion valve 120 has transitioned to the passage state from the collection state, the system 100 may be reset. In some embodiments, the system 100 may be reset by removing the collection canister 140 including the fluid sample. Once the collection canister 140 has been removed, the diversion valve 120 may transition back to the collection state and either the collection canister 140 may be reattached to the system 100 or a new collection canister 140 may be attached to the system 100.

Figure 3A:
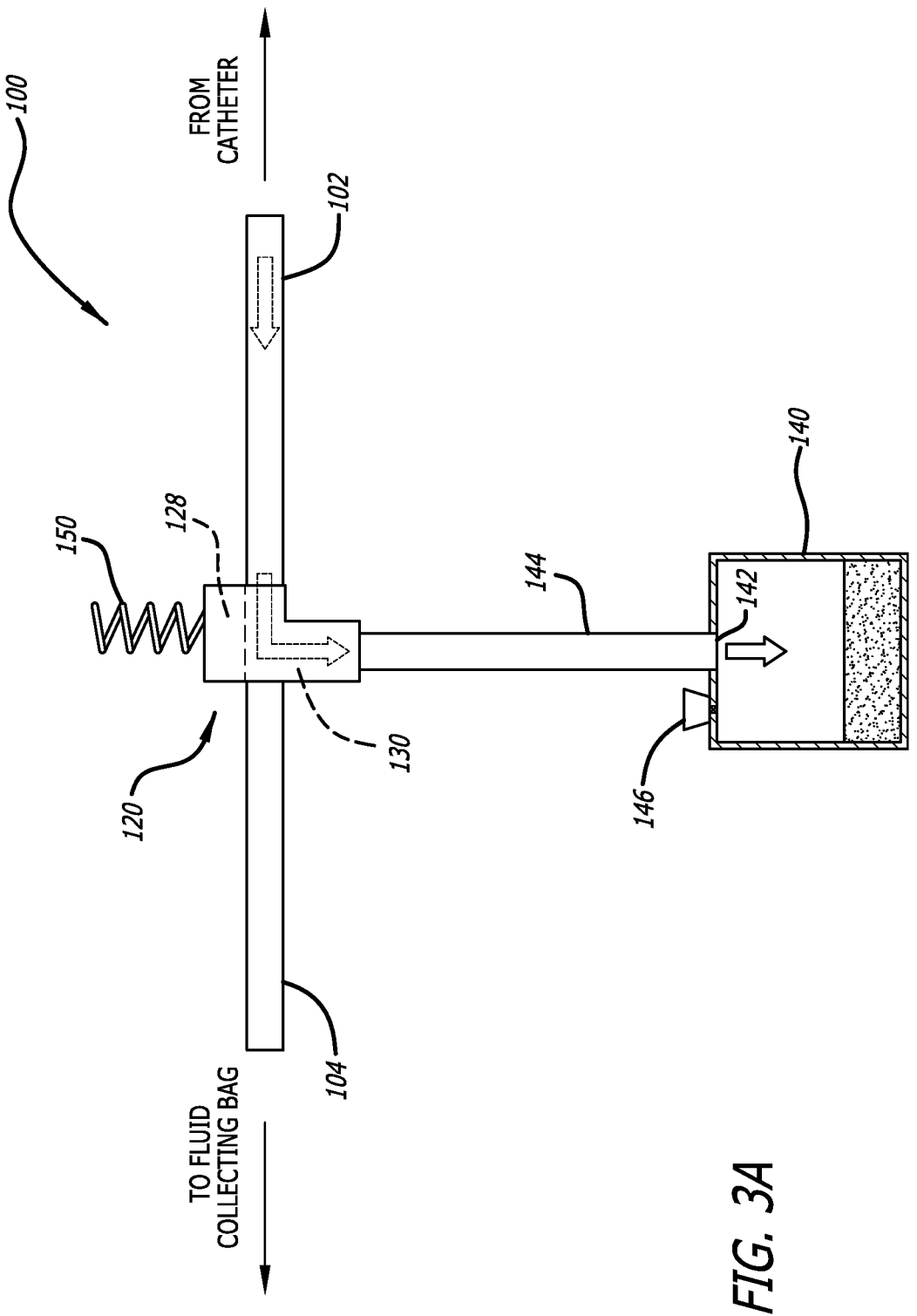
FIGS. 3A-3B illustrate a cross sectional view an exemplary method of collecting a fluid sample using the fluid sample collection system, in accordance with some embodiments.
Figure 3B:
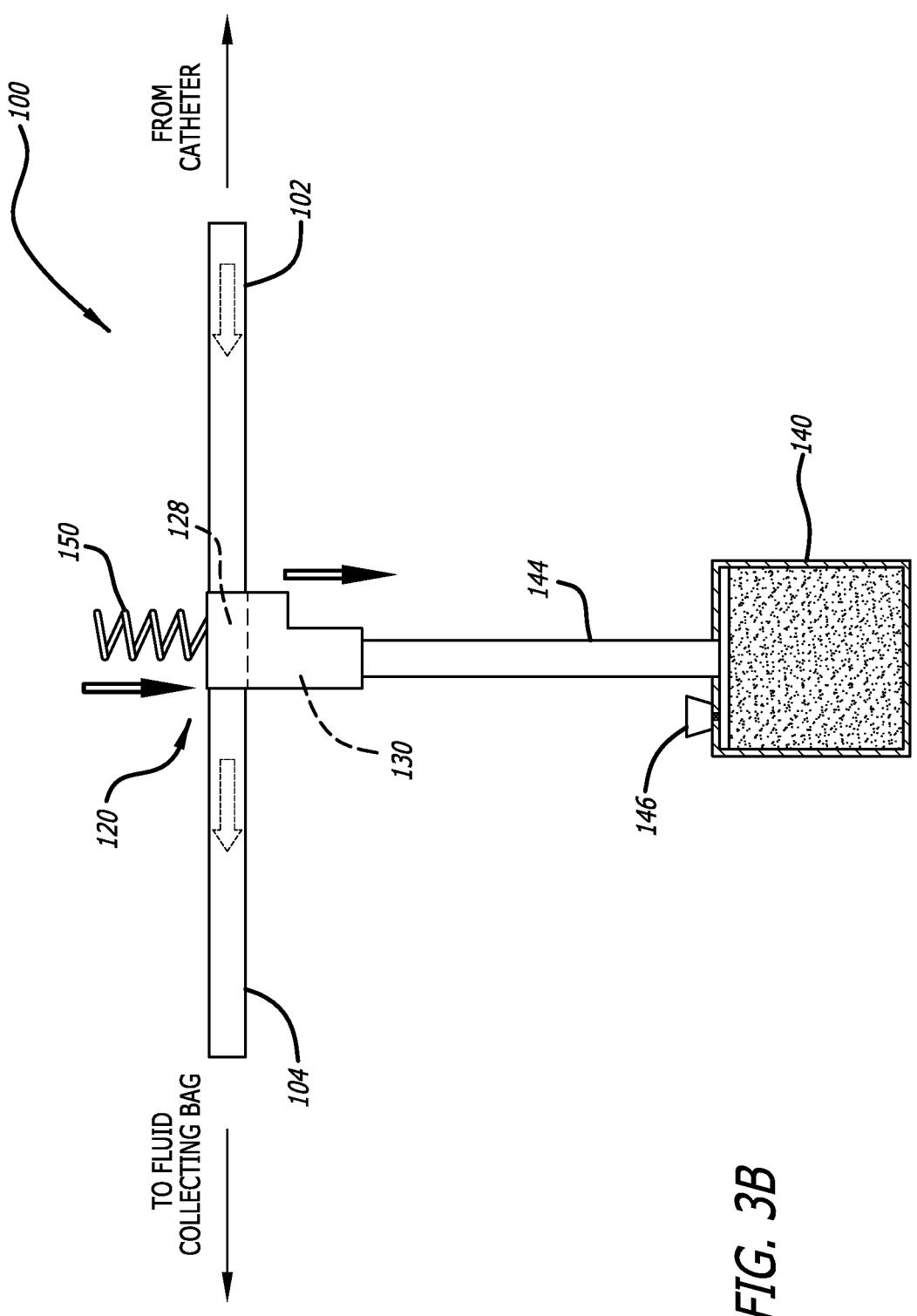

FIGS. 3A-3B illustrate a cross sectional view of an exemplary method of collecting a fluid sample using the fluid sample collection system 100, in accordance with some embodiments. In some embodiments, the system 100 includes the diversion valve 120, configured to transition between the collection state and the passage state. The diversion valve 120 is configured to be in fluid communication with the first fluid line 102 coupled to a catheter, the second fluid line 104 coupled to the fluid collecting bag and the fluid channel 144 coupled to the collection canister 140. In some embodiments, the spring 150 may be biased towards the collection state. A volume of fluid may be passed through the first fluid line 102 to the diversion valve 120 with the diversion valve 120 in the collection state. The collection channel 130 may direct the volume of fluid to the collection canister 140. As illustrated in FIG. 3B, once the collection canister 140 has been filled with the fluid sample, the weight of fluid sample within the collection canister 140 may allow the spring 150 to expand transversely downward, transitioning the diversion valve 120 to the passage state, allowing an additional volume of fluid from the first fluid line 102 to bypass the collection canister 140, to be received by the second fluid line 104. Advantageously, the collection of the fresh fluid sample does not require additional human interaction and does not interrupt the patient's ability to void fluid.

Figure 4:
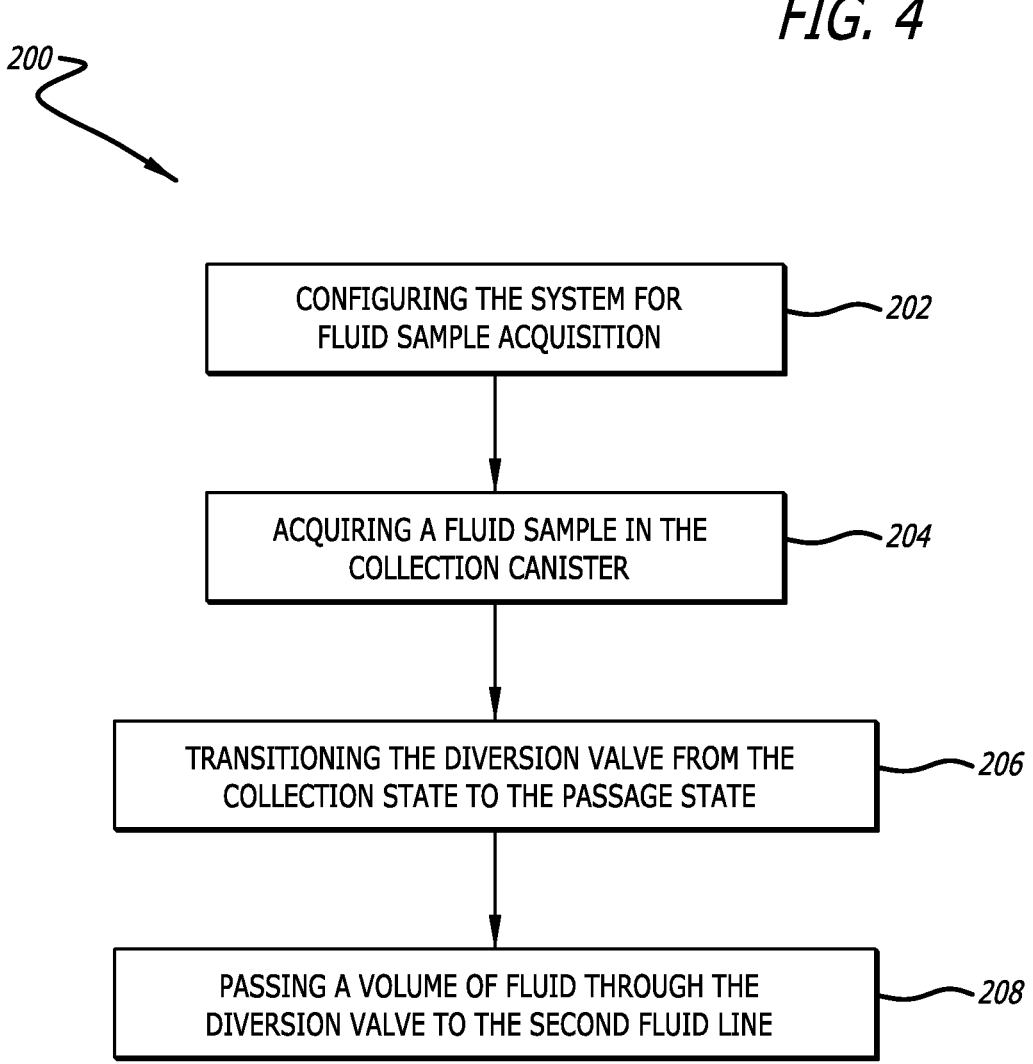
FIG. 4 illustrates a flow chart of the exemplary method of collecting a fluid sample from a patient without human interaction, in accordance with some embodiments.

FIG. 4 illustrate a flow chart of the exemplary method 200 of collecting a fresh fluid sample from a patient without human interaction, in accordance with some embodiments. In some embodiments, human interaction includes a clinician interrupting a patient's ability to void a volume of fluid to acquire a fluid sample. In some embodiments, the method 200 includes configuring the system 100 for fluid sample acquisition (block 202). In some embodiments, configuring includes coupling the spring 150 to the stabilizing structure. In some embodiments, configuring includes suspending the diversion valve 120 from the spring 150. In some embodiments, configuring includes ensuring the diversion valve 120, the fluid channel 144 and the collection canister 140 are in an upright position. In some embodiments, configuring includes coupling the first fluid line 102 in fluid communication with a catheter and the second fluid line 104 in fluid communication with a fluid collection bag to the diversion valve 120. In some embodiments, configuring includes confirming the diversion valve 120 is in the collection state.

The method 200 includes acquiring a fresh fluid sample in the collection canister 140 (block 204). In some embodiments, acquiring a fluid sample includes acquiring a fluid sample with the diversion valve 120 in the collection state. The collection state is as described above with the spring 150 being compressed relative to the passage state, the collection channel 130 receiving the volume of fluid from the first fluid line 102 and directing the volume of fluid through the fluid channel 144 to the collection canister 140. In some embodiments, acquiring a fluid sample includes acquiring a volume of fluid. In some embodiments, acquiring a fluid sample includes acquiring the fluid sample by gravity flow. In some embodiments, acquiring a fresh fluid sample in the collection canister 140 includes acquiring a fresh fluid sample in the collection canister 140 until the collection canister 140 is partially or completely full. In some embodiments, acquiring a fresh fluid sample in the collection canister 140 includes indicating to a clinician by a signaling system, that a fluid sample has been collected.

The method 200 includes transitioning the diversion valve 120 from the collection state to the passage state using the weight of fluid sample in the collection canister 140 (block 206). In some embodiments, the weight of the fluid sample within the collection canister 140 stretches the spring 150 relative to the collection state, transitioning the diversion valve 120 from the collection state to the passage state. The passage state is as described above with the string 150 stretched under the weight of the fluid sample in the collection canister 140 and the passage channel 128 directing fluid from the first fluid line 102 to the second fluid line 104. The method 200 includes passing a volume of fluid through the diversion valve 120 to the second fluid line 104 (block 208).

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A fluid sample collection system, comprising:
a diversion valve defining a cavity and having a distal opening disposed in a distal side, and a proximal opening disposed in a proximal side, each of the distal opening and the proximal opening communicating with the cavity;
a diversion valve housing slidably engaged with the cavity along a transverse axis between a collection state and a passage state, the diversion valve defining a passage channel extending longitudinally between a proximal opening and a distal opening, and a collection channel defining an angled central axis extending between the distal opening and a bottom opening, the diversion valve housing biased towards the collection state; and
a collection canister coupled to a bottom side of the diversion valve housing and in fluid communication with the bottom opening of the collection channel, the collection channel of the diversion valve housing in the collection state directing a fluid flow to the collection canister until a volume of fluid accumulated within the collection canister increases a weight of the collection canister to move the diversion valve housing along the transverse axis and transition the diversion valve housing to the passage state.

2. The fluid sample collection system according to claim 1, further including a first fluid line coupled to the distal opening of the diversion valve to provide fluid communication between a catheter and the cavity of the diversion valve.

3. The fluid sample collection system according to claim 2, further including a second fluid line coupled to the proximal opening of the diversion valve to provide fluid communication between the cavity of the diversion valve and a fluid collection bag.

4. The fluid sample collection system according to claim 3, wherein the diversion valve housing in the collection state aligns a collection channel distal opening with the distal opening of the diversion valve to direct the fluid flow from the catheter into the collection canister.

5. The fluid sample collection system according to claim 3, wherein the diversion valve housing in the passage state aligns the distal opening of the passage channel with the distal opening of the diversion valve and the proximal opening of the passage channel with the proximal opening of the diversion valve to direct the fluid flow from the catheter to the fluid collection bag.

6. The fluid sample collection system according to claim 1, further including a spring coupled to the diversion valve housing to bias the diversion valve housing to the collection state, and wherein the weight of the collection canister overcomes a force exerted on the diversion valve housing by the spring to transition the diversion valve housing to the passage state.

7. The fluid sample collection system according to claim 6, wherein the volume of fluid is one of a 30 ml volume, a 60 ml volume, or a 90 ml volume.

8. The fluid sample collection system according to claim 6, wherein the spring transitions to a relatively stretched configuration as the diversion valve housing transitions from the collection state to the passage state.

9. The fluid sample collection system according to claim 6, wherein the spring transitions to a relatively compressed configuration as the diversion valve housing transitions from the collection state to the passage state.

10. The fluid sample collection system according to claim 1, further including a fluid channel configured to couple the collection canister with the bottom side of the diversion valve housing and provide fluid communication between the bottom opening of the collection channel and the collection canister.

11. The fluid sample collection system according to claim 10, wherein the collection canister is detachably coupled to the fluid channel to allow for selective removal of the collection canister.

12. The fluid sample collection system according to claim 1, wherein the collection canister includes a hydrophobic vent configured to allow a gas to exit an interior of the collection canister.

13. The fluid sample collection system according to claim 1, wherein the collection canister includes a floater disposed within an interior of the collection canister and is configured to block an opening of the collection canister when the volume of fluid is disposed within the collection canister.

14. The fluid sample collection system according to claim 13, wherein the collection canister further includes a signaling system configured to indicate when the volume of fluid is disposed within the collection canister.

15. A method of collecting a fluid sample from a patient, comprising:

providing a diversion valve defining a cavity and includ-
ing a diversion valve housing slidably engaged with the
cavity;

transitioning the diversion valve housing to a collection
state by a spring applying a force to the diversion valve
housing, to align a distal opening of a collection
channel with a distal opening of the diversion valve;

directing a fluid flow from a catheter that is in fluid
communication with the distal opening of the diversion
valve through the collection channel and into a collec-
tion canister;

collecting a predetermined volume of fluid within the
collection canister to increase a weight of the collection
canister, the weight increase applying a greater force to
the diversion valve housing than the force of the spring,
wherein the weight increase transitions the diversion
valve housing to a passage state to align a distal
opening of a passage channel with the distal opening of
the diversion valve and to align a proximal opening of
the passage channel with the proximal opening of the
diversion valve; and directing the fluid flow from the catheter to the proximal
opening of the diversion valve that is in fluid commu-
nication with a collection bag.

16. The method according to claim 15, further including
providing fluid communication between the catheter and the
distal opening of the diversion valve by a first fluid line, and
providing fluid communication between the proximal open-
ing of the diversion valve and the collection bag by a second
fluid line.

17. The method according to claim 15, further including
blocking an opening of the collection canister that is in fluid
communication with a bottom opening of the collection
channel when the predetermined volume of fluid is disposed
within the collection canister.

18. The method according to claim 17, further including
detaching the collection canister from a fluid channel that
provides fluid communication between the bottom opening
of the collection channel and the collection canister.

* * * * *